July 20, 1937. M. R. JACOBUS Plant Pat. 257
HYBRID PERPETUAL ROSE
Filed July 20, 1935
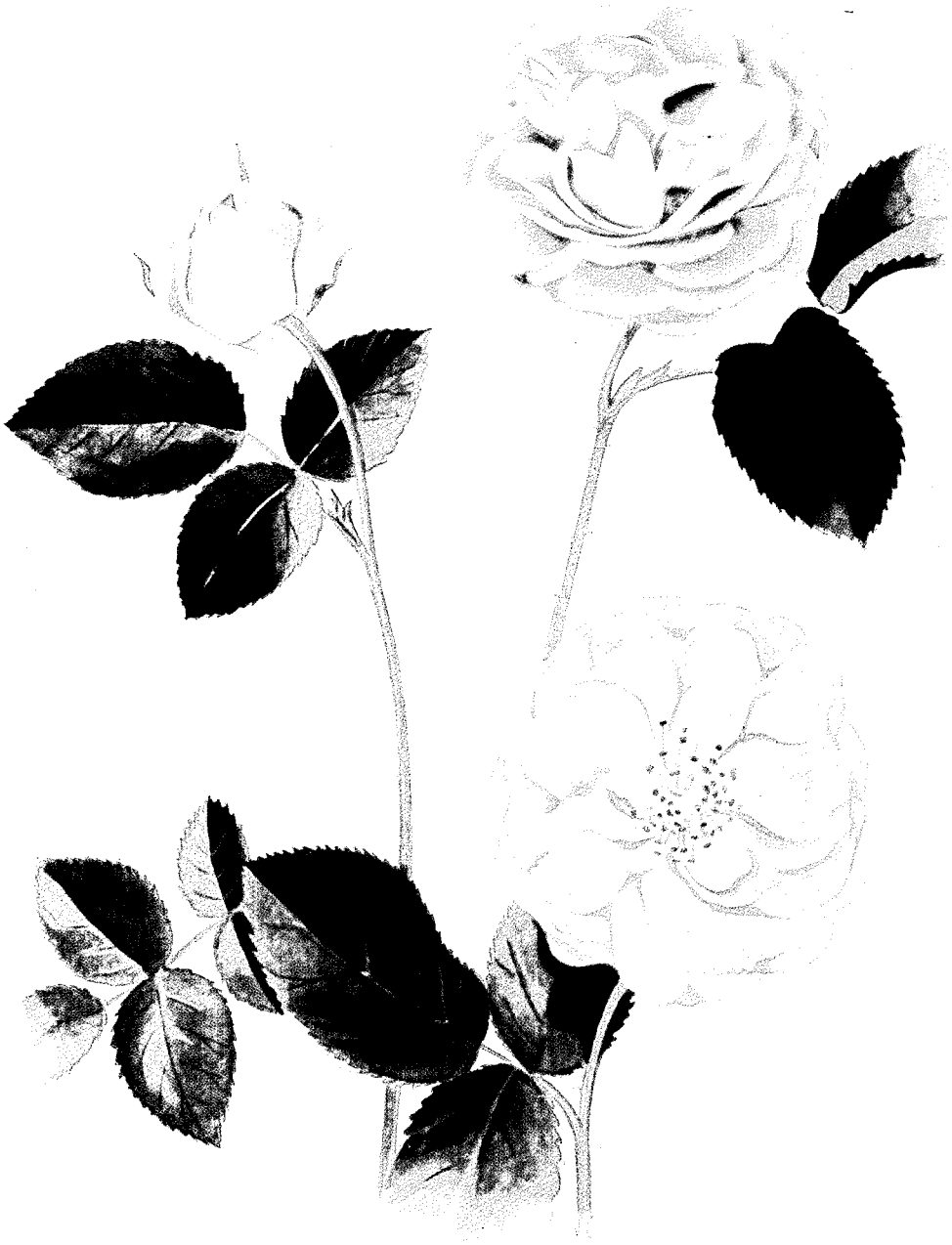
INVENTOR
MARTIN R. JACOBUS
BY Fred K. Schmitz
ATTORNEY Patented July 20, 1937

Plant Pat. 257

UNITED STATES PATENT OFFICE

257

HYBRID PERPETUAL ROSE

Martin R. Jacobus, Ridgefield, N. J.

Application July 20, 1935, Serial No. 32,335

1 Claim. (Cl. 47—61)

The invention relates to improvements in hybrid roses, and it has for its object to produce a new rose possessing exceptional fragrance and pleasing color and form, as well as possessing good lasting qualities, and being also a vigorous grower.

In the drawing accompanying this application, the novel rose is shown in its natural colors as a bud, partly opened; as a blossom well opened; and as a fully opened flower.

The novel rose is a seedling and was developed at Ridgefield, New Jersey, with cross-pollination between *Rosa damascena* as the seed parent and Souvenir de Claudius Pernet as the pollen carrier. After pollination, the seeds were collected and planted; and, from a resulting plant, buds were made upon wild rose stock such as *Rosa canina, Rosa multiflora,* etc.; also, slips were taken therefrom.

The plant is of large size and an upright shrub and vigorous grower, stronger than the *Rosa damascena,* with canes attaining a height in excess of six feet and moderately thorny. It may be grown both in and out of greenhouses from buds, slips or grafts. As to blooming properties, it may be classed as abundant to profuse.

The novel rose blossoms singly on a relatively long, strong stem and as a rule but once during a season—about the first half of June. The bud opens well and the bloom is double and its fragrance is unusual, being almost equal to that of the *Rosa damascena,* its seed parent. It possesses the high colors of the Austrian Copper rose, with the exception that at the base of its round, imbricated petals and extending some distance upwardly therefrom yellow predominates and merges into the copper-red or rose color of the novel rose. This yellow coloring is more apparent at the back of the petals and particularly in the bud than when the bloom is fully opened. The bud is of medium size and tends to globular form upon opening, the copper-red color appearing after the sepals divide and as the petals unfold. It is borne on a stiff peduncle of medium length.

There is thus secured in the novel rose the color of the Austrian Copper, modified to some extent, together with the fragrance of the Damask rose with fully double bloom of good size.

The foliage which is oval-pointed is dark green, glossy and abundant, comprising three to seven leaflets of large size with the serrations somewhat sharper than in the case of the parent, *Rosa damascena*; and on the underside the leaflets are of a lighter green, less glossy and with thorns along the midrib.

The rose is of a heavy double type with good lasting qualities so that its pistil and stamens are not visible until the rose is fully opened, as indicated. When fully opened with open center, the diameter of the bloom is approximately 3½ to 4 inches and the bloom is of somewhat flattened form, the petals curling back only slightly and retaining substantially the form of the rose until the petals drop off. The fruit is large and self-fertilizing.

The novel rose may be specifically characterized as follows, Ridgway standard:

In the fully opened rose, the outside upper half of the petals is ivory yellow—Plate XXX—21-*f*—shading to a color between sulphur yellow and pale greenish yellow, Plate V—25-*f* and V—25-*d*.

The inside upper half is pale rosalene purple—Plate XXVI—69-*d*, shading to cream buff, XXX—19-*d*, at the base.

With respect to the intermediate petals, the outside shades from Marguerite yellow—Plate XXX—23-*f*, through primrose yellow, Plate XXX—23-*d*, to pale greenish yellow, Plate V—25-*d*, at the base.

The inside of the intermediate petals shades from Venetian pink at apex, Plate XIII—1-*f*, through rose-pink, Plate XII—71-*f*, to pale green-yellow, Plate V—27-*f*.

With respect to the inside petals, the outside shades from Marguerite yellow, Plate XXX—23-*f*, through primrose yellow, Plate XXX—23-*d*, to pale greenish yellow, Plate V—25-*d*, at the base.

The general effect of the opening bud is seashell pink, Plate XIV—11-*f*, and carrot red, Plate XIV—7-*b*; and the color of the outside edge of the outside petals is mallow pink, Plate XII—67-*f*, with central portion pale greenish yellow, Plate V—25-*d*, with light greenish yellow, Plate V—25-*b*, at the base.

The intermediate petals at the apex are of a pale flesh color, Plate XIV—7-*f*; middle portion, maize yellow, Plate IV—19-*f*; base, picric yellow, Plate IV—23-*d*; while the inner petals at the apex are of a jasper pink, Plate XIII—3-*d*; middle portion, buff yellow, Plate IV—19-*d*; base, pale lemon yellow, Plate IV—23-*b*.

The shape of the petals in the case of a fully open rose is, with respect to the outside petals, round, notch in apex; intermediate petals, oval, notch in apex; inside petals, narrow oval, somewhat moon-shaped.

With bud just opening, the outside petals are somewhat broadly obovate, apex roughly dentate; intermediate petals, oval, apex slightly notched; inner petals, half moon shape.

The number of petals have been variously determined as 47, 57, 73.

The blooms average 3½ inches across, with fairly full center, and finally opening rather flat, showing the stamens which are many; and the filaments are red, long; anthers, broad, brown-edged, yellow-centered.

The pistils also are many, stiles long, protruding from hip, stigmas large yellow. Rudimentary hip nearly round.

The bud is round, with the five sepals extending beyond it as foliaceous appendages, and six or more appendages on margins and on foliaceous tips of sepals; also a few hairs on surface and margins.

The petals are moderately thick, satiny, and drop cleanly.

The foliage is abundant, leathery; of five large oval leaflets of dark dull yellow green, Plate XXXII—31-*m*, coarsely serrate, almost dentate, with a few prickles on under side of rachis.

The thorns are abundant, rather slender, red on young wood, gray on old wood, old wood dark brown.

The plant itself is bushy, vigorous, moderately well-branched, of strong stems, flowers usually borne singly on 5-inch to 9-inch branches, while the leaflets are rough, especially above.

The stipules are narrow, long, acute, and turned out at an angle of 45°.

The new foliage and the shoots are green.

I claim:

A hybrid perpetual rose as shown and described and characterized by a yellowish copper-red bud of medium size tending to globular form, and the bloom being double, of good size, possessing lasting qualities and intensely fragrant, having the odor of *Rosa damascena,* with the high color generally of the Austrian Copper rose except at the base and back of the petals where yellow predominates and merges into the copper-red color of the bloom proper; and the foliage being abundant, of large size, more glossy than that of *Rosa damascena,* and of a dark green color with three, five and seven leaflets having sharper serrations than *Rosa damascena,* the canes of the plant being moderately thorny and of vigorous, superior growing qualities, attaining a height in excess of six feet.

MARTIN R. JACOBUS.